United States Patent
Brandt et al.

(10) Patent No.: US 7,275,982 B1
(45) Date of Patent: Oct. 2, 2007

(54) OZONE-BASED CONVEYOR CLEANING SYSTEM

(75) Inventors: Jim Brandt, Bainbridge, WA (US); Jonathan Brandt, Bainbridge, WA (US)

(73) Assignee: Ozone International, LLC, Bainbridge Island, WA (US)

(*) Notice: Subject to any disclaimer, the term of this patent is extended or adjusted under 35 U.S.C. 154(b) by 0 days.

(21) Appl. No.: 11/383,103

(22) Filed: May 12, 2006

(51) Int. Cl.
A22C 25/08 (2006.01)

(52) U.S. Cl. .................................................. 452/177

(58) Field of Classification Search ............... None
See application file for complete search history.

(56) References Cited

U.S. PATENT DOCUMENTS

| | | | |
|---|---|---|---|
| 3,612,094 A | 10/1971 | Hare et al. | |
| 4,309,388 A * | 1/1982 | Tenney et al. | 422/304 |
| 4,325,753 A | 4/1982 | Baur | |
| 4,549,477 A * | 10/1985 | McCabe, Jr. | 99/477 |
| 5,236,512 A | 8/1993 | Rogers et al. | |
| 5,493,754 A | 2/1996 | Gurstein et al. | |
| 5,502,988 A | 4/1996 | Shimazaki et al. | |
| 5,503,594 A | 4/1996 | Karubian et al. | |
| 5,815,869 A | 10/1998 | Hopkins | |
| 5,839,155 A | 11/1998 | Berglund et al. | |
| 5,858,435 A * | 1/1999 | Gallo | 426/320 |
| 5,865,995 A | 2/1999 | Nelson | |
| 5,868,945 A | 2/1999 | Morrow et al. | |
| 5,882,253 A * | 3/1999 | Mostoller | 452/173 |
| 6,115,862 A | 9/2000 | Cooper et al. | |
| 6,233,966 B1 * | 5/2001 | Delpuech et al. | 62/374 |
| 6,264,543 B1 * | 7/2001 | Garcia et al. | 452/141 |
| 6,348,227 B1 | 2/2002 | Caracciolo, Jr. | |
| 6,361,688 B1 | 3/2002 | Nelson | |
| 6,379,633 B1 | 4/2002 | Garlick | |
| 6,455,017 B1 | 9/2002 | Kasting, Jr. et al. | |
| 6,458,398 B1 | 10/2002 | Smith et al. | |
| 6,565,927 B1 * | 5/2003 | Drzal et al. | 427/487 |
| 6,638,364 B2 | 10/2003 | Harkins et al. | |
| 6,683,312 B2 * | 1/2004 | Yun | 250/455.11 |
| 6,692,784 B2 * | 2/2004 | Davidson | 426/298 |
| 6,736,716 B1 * | 5/2004 | Sugiyama | 452/2 |
| 6,803,066 B2 * | 10/2004 | Traeder et al. | 426/333 |
| 6,964,788 B2 * | 11/2005 | Phebus et al. | 426/335 |
| 7,067,089 B2 * | 6/2006 | Wen | 422/292 |
| 2005/0161433 A1 | 7/2005 | Silberberg et al. | |

* cited by examiner

Primary Examiner—Thomas Price
(74) Attorney, Agent, or Firm—Black Lowe & Graham, PLLC

(57) ABSTRACT

A conveyor cleaning system includes a treating region, a processing region, and a conveyor belt traveling from the treating region to the processing region. A distributor positioned across the treating region deposits a film of ozonated water on the conveyor belt. In the processing region, the conveyor belt is exposed to soiling agents such as grease and other animal matter. A high-pressure rinser may be positioned over the treating section such that the distributor is positioned between the high-pressure rinser and the processing region. Ozonated water may be generated by a system including first and second tanks. The first tank is filled with ozone gas and water. After a predetermined time, undissolved ozone gas is released. The contents of the first tank are then transferred to a second tank along with more ozone gas. After waiting a predetermined time period, undissolved ozone gas is released from the second tank.

8 Claims, 3 Drawing Sheets

OZONE-BASED CONVEYOR CLEANING SYSTEM

FIELD OF THE INVENTION

This invention relates generally to conveyor belts and, more specifically, to cleaning systems for conveyor belts.

BACKGROUND OF THE INVENTION

Meat processing factories must be kept extremely clean in order to ensure a safe, clean final product. The United States Department of Agriculture (USDA) strictly enforces regulations requiring meat-processing facilities to maintain proper cleanliness. On-site inspectors will often verify compliance by evaluating both the presence of microbes and the aesthetic appearance of a plant.

In the typical prior plant, conveyor belts and tools are cleaned periodically. In such plants, the entire plant is often shut down in order to thoroughly clean. However, in the periods between cleanings, grease and other soiling materials are allowed to collect and become compacted on the equipment, particularly in recesses, such as surface scratches and the joints between members forming the equipment. This collection of soil and grease is extremely unsanitary and degrades the aesthetic appearance of the plant. Plant operators therefore risk being reprimanded, fined, or shut down by the on-site USDA inspector. Furthermore, the longer the grease and soil is allowed to remain on the equipment, the more time and effort is required to remove it. Typically, the use of chemical solvents and hot water is required. These solvents are typically unsafe for human consumption and therefore equipment must be thoroughly rinsed before meat products may contact it.

In view of the foregoing, it would be an advancement in the art to provide a system allowing uninterrupted operation of a meat processing facility for extended periods while still maintaining a low microbial count and good aesthetics, without the use of hazardous chemicals.

SUMMARY OF THE INVENTION

A conveyor cleaning system is disclosed enabling continuous operation of meat processing equipment without the use of chemical solvents. In one embodiment, a conveyor system has a treating region and a processing region. A distributor positioned across the treating region deposits a film of ozonated water on the conveyor belt. In the processing region, the conveyor belt is exposed to soiling agents such as grease and other animal matter.

A high-pressure rinser may also be positioned over the treating section such that the distributor is positioned between the high-pressure rinser and the processing region. The rinser removes grease and soil prior to deposition of a fresh layer of ozonated water on the conveyor belt.

Ozonated water may be generated by a system including first and second tanks. The first tank is filled with ozone gas and water. After a predetermined time, such as one minute, undissolved ozone gas is released. The contents of the first tank are then transferred to a second tank along with more ozone gas. After again waiting a predetermined time period, such as one minute, undissolved ozone gas is released from the second tank. The contents of the second tank may then be used to coat the conveyor belt and for other purposes.

BRIEF DESCRIPTION OF THE DRAWINGS

Preferred and alternative embodiments of the present invention are described in detail below with reference to the following drawings.

DETAILED DESCRIPTION OF THE PREFERRED EMBODIMENT

Figure 1:
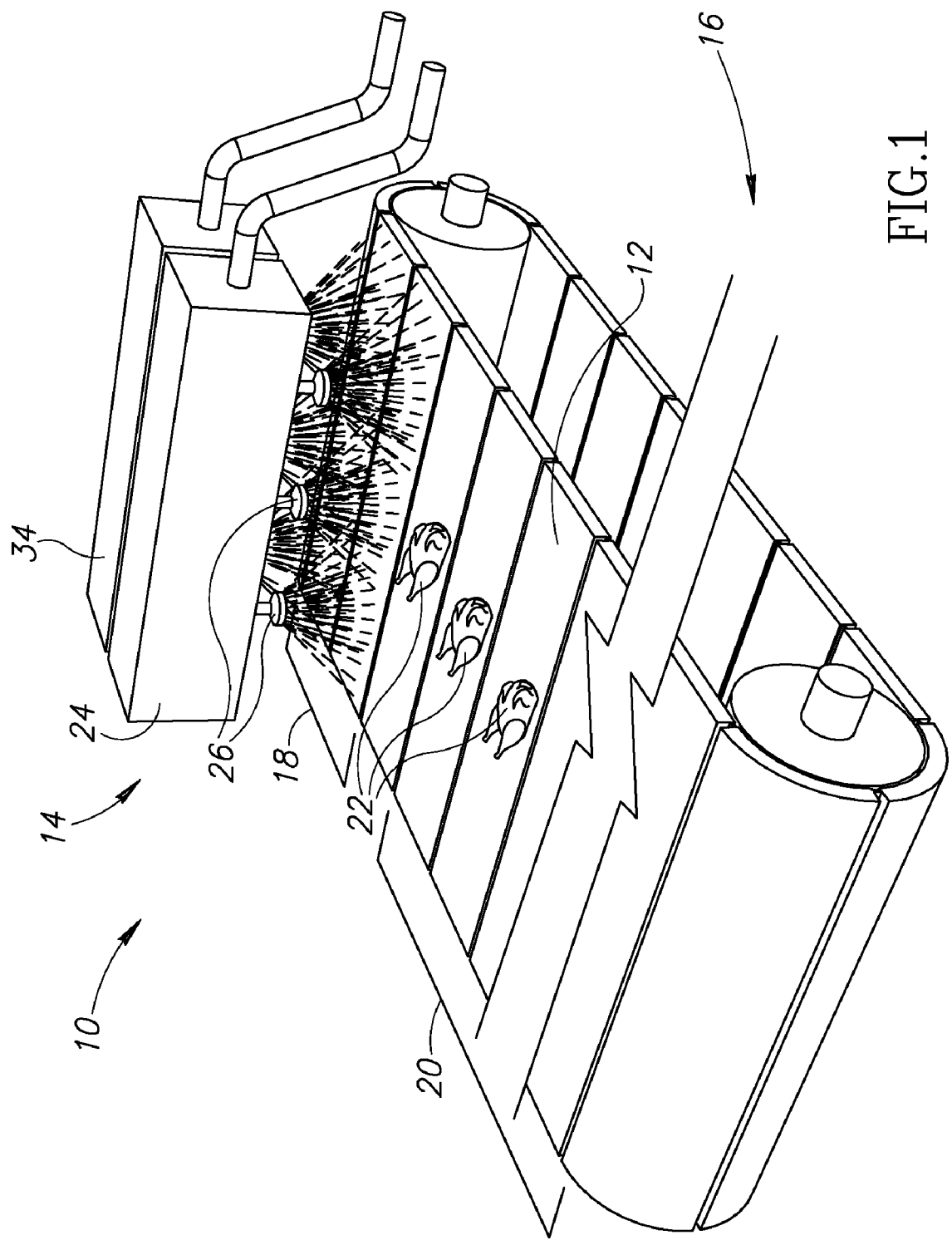
FIG. 1 is perspective view of a conveyor treating system, in accordance with an embodiment of the present invention.

Referring to FIG. 1, a conveyor treating system 10 includes a conveyor belt 12 and a distributor 14. The conveyor belt 12 travels in direction 16 from a treating region 18 to a processing region 20. A distributor 14 located proximate the treating region 18 deposits a layer of ozonated water on the conveyor belt 12. In the processing region 20, animal carcasses 22, and other meat products are deposited on the conveyor belt 12.

The distributor 14 may be embodied as a sprayer 24 having multiple heads 26 for spraying ozonated water across substantially the entire width of the conveyor belt 12. In the illustrated embodiment, the sprayer 24 includes heads 26 emitting a jet of water from 10 to 110 degrees wide at a rate of from 0.25 to 5 gallons per minute (gpm). The spray patterns of the heads 26 may overlap to ensure complete coverage. The heads 26 are typically located from 2 to 12 inches from the surface of the conveyor belt 12.

The ozonated water used typically has a temperature from 32 to 100 degrees F. The concentration of ozone within the ozonated water is chosen such that off-gas from the nozzles remains below safety thresholds. In the illustrated embodiment, at the point of impact with the conveyor belt 12, the ozonated water typically has an ozone concentration of from 1.8 to 3.5 parts per million (ppm). The pressure of the ozonated water is typically low to reduce the amount of off-gassing. Typical pressures used include from 10 to 110 psi.

Figure 2:
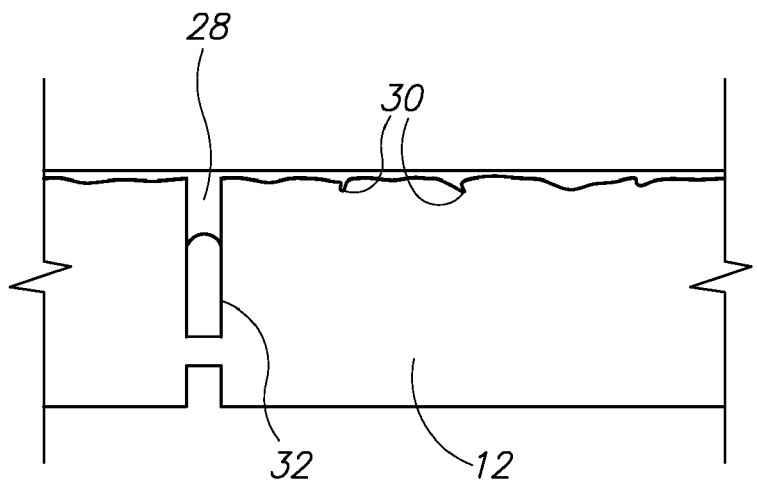
FIG. 2 is a side cross-sectional view of a conveyor belt bearing an ozonated water layer, in accordance with an embodiment of the present invention.

Referring to FIG. 2, after leaving the treating region 18, the conveyor belt 12 bears a film 28 of ozonated water. Through capillary action, the ozonated water is drawn into surface cracks 30, gaps 32, and other recesses in the conveyor belt. As the belt enters the processing region 20, grease and soil contacting the belt will contact the film 28, causing the grease and soil to break down rather than adhere to the belt. In particular, grease and soil entering cracks 30 and gaps 32 will be either displaced or broken down by the ozonated water present. In this manner, grease and soil does not collect or compact on the conveyor belt 12 or within recesses in the belt.

This advantageous breaking down of grease prior to compaction or drying is accomplished without the use of solvents or other agents that are unsafe for human consumption. Ozone rapidly breaks down into oxygen, leaving no unsafe residue. Furthermore, only a thin film of ozonated water remains on the belt 12 as it enters the processing region 20. Workers are therefore only subject to insignificant amounts of ozone.

The grease and soil broken down by the ozonated water is easily rinsed away in the treating region 18 by the distributor 14 or a distinct rinsing sprayer 34. The rinsing sprayer 34 may direct a high-pressure jet of non-ozonated water at the conveyor belt 12 preparatory for the deposition of ozonated water by the distributor 14. The rinsing sprayer 34 may spray water at pressures from 100 to 1000 psi. Inasmuch as the water emitted from the rinsing sprayer 34 is non-ozonated the jet of water may be at a much higher pressure to more effectively remove grease and soil without risk of off-gassing. In order to reduce off-gassing, the spray pattern from the distributor 14 preferably will not overlap that of the high-pressure rinsing sprayer 34.

The above system may be used to treat other equipment in the meat processing industry, such as slicers, saws, and the like.

Figure 3:
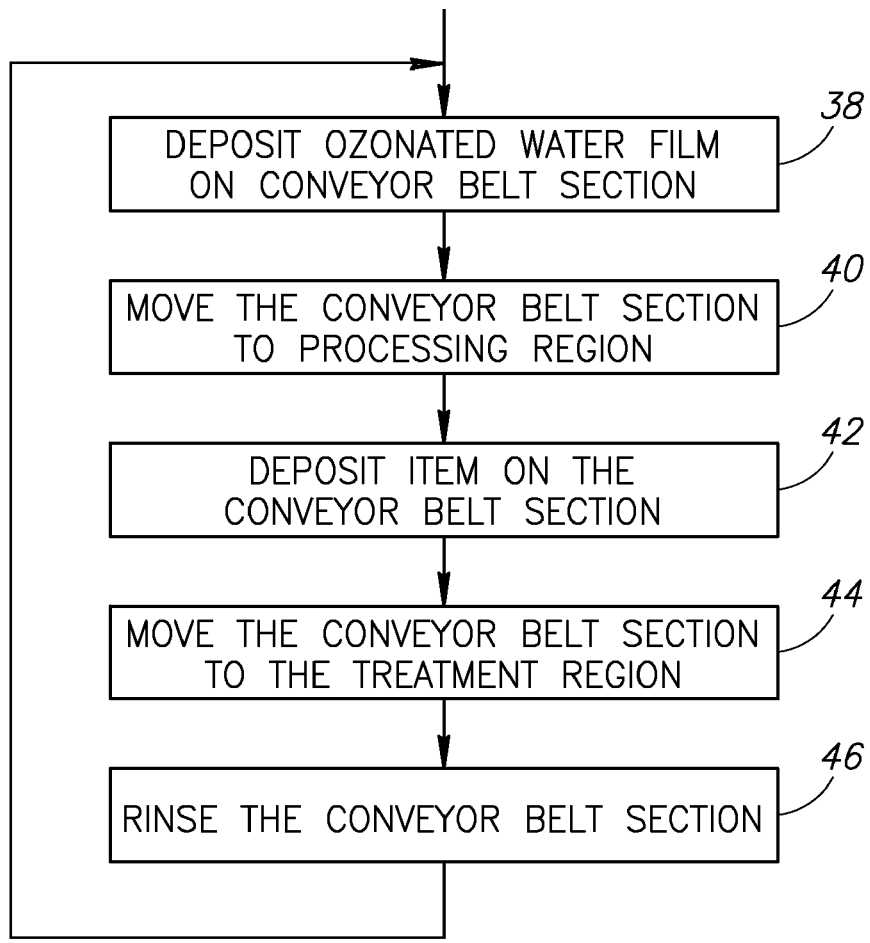
FIG. 3 is a process flow diagram of a preferred method of employing the embodiment of FIG. 1.

The conveyor treating system 10 may be used to perform the method 36 of FIG. 3. Ozonated water is deposited on a section of the conveyor belt 12 at block 38. The deposited ozonated water may form a film 28. The conveyor belt section is then moved to the processing region 20 at block 40. Items, such as animal carcasses and cuts of meat, are deposited on the conveyor belt section at block 42 for processing. At block 44, the conveyor belt section is brought back to the treating region 18. The conveyor belt section is rinsed at block 46. The process 36 is then repeated.

The systems and methods disclosed above enable an 80 to 100% reduction in sanitation chemicals used in a typical meat processing plant. They also reduce by 80 to 100% the amount of hot water required for sanitation. The labor required to sanitize the meat processing plant has also been reduced by 50%.

Furthermore, the system disclosed is more effective than conventional systems. Surfaces treated as described above have a 50% lower bacteria count. Continuous operation of the processing plant is also enabled inasmuch as grease and soil is not allowed to compact on equipment. Plants treated as described above may be safely operated 24 hours a day under USDA supervision. Inasmuch as the conveyor belt 12, or other equipment, is constantly cleaned, degradation of aesthetics between cleanings is significantly reduced.

Figure 4:
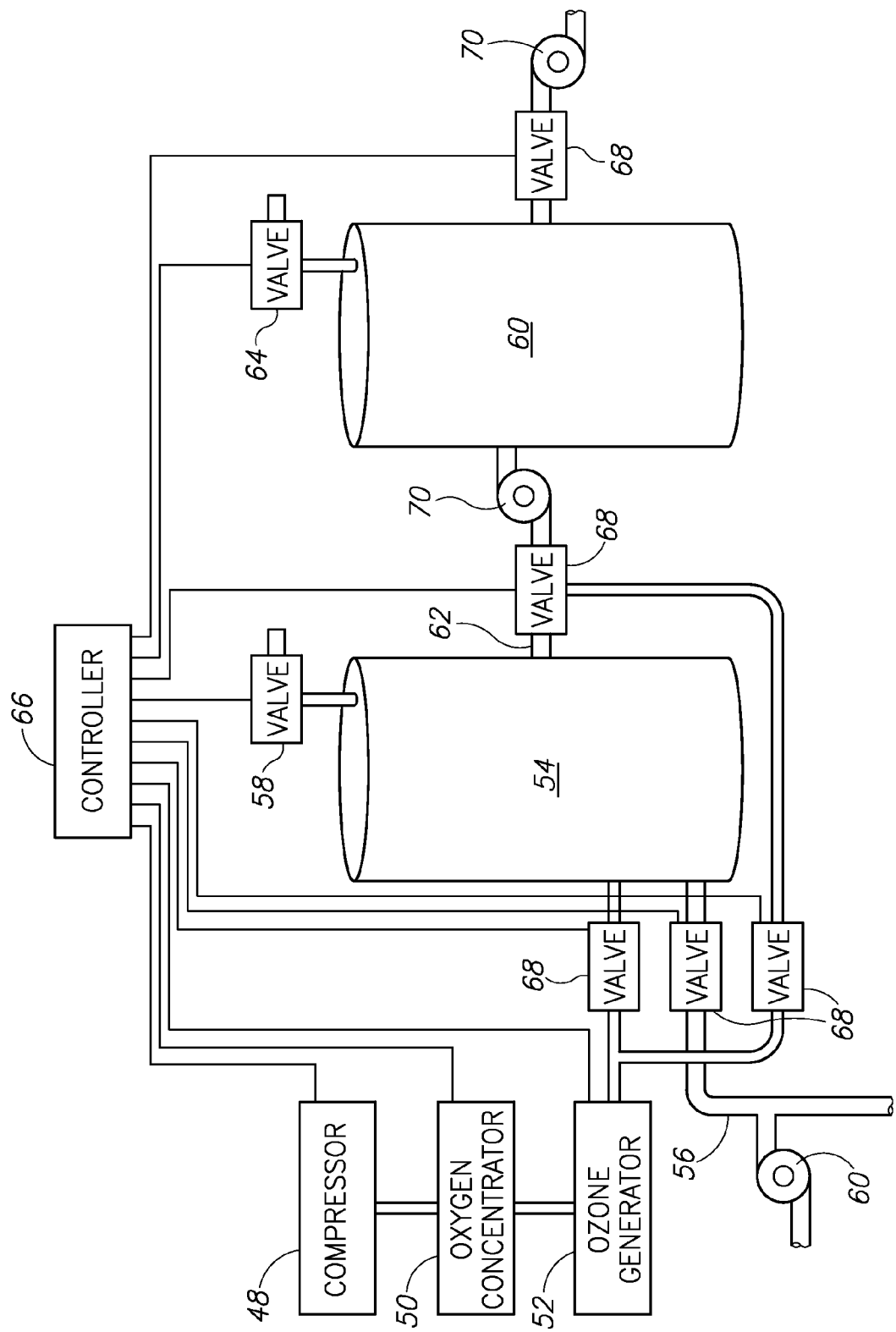
FIG. 4, is a schematic diagram of an ozonated water generating system, in accordance with an embodiment of the present invention.

Ozonated water for use in the conveyor treating system 10 may be produced using the generating system of FIG. 4. Ambient air is compressed by a compressor 48. The oxygen in the compressed air is then extracted by an oxygen concentrator 50. A portion of the oxygen, typically between 2 and 15% by weight, is converted into ozone by an ozone generator 52.

Ozone from the ozone generator 52 is fed into a tank 54 along with non-ozonated water. The ozone may be fed into an inlet pipe 56 conducting water to the tank 54. Alternatively, the ozone and water may enter the first tank 54 through distinct openings. In order to avoid excessive ozone levels, ozone left undissolved after a predetermined period is released, such as through a release valve 58. In one preferred embodiment, undissolved ozone is released after from 0.5 to 1.5 minutes. In another preferred embodiment, undissolved ozone is released after one minute.

Ozonated water from the first tank may be emptied into a second tank 60. Ozone may also be injected into the second tank 60, whether through a distinct inlet or through an inlet tube 62 connecting the second tank 60 to the first tank 54.

As with the first tank 54, undissolved ozone is released after a predetermined period by means of a release valve 64. In one preferred embodiment, undissolved ozone is released after from 0.5 to 1.5 minutes. In another preferred embodiment, undissolved ozone is released after one minute. The ozonated water in the second tank 60 is then used for purposes such as coating a conveyor belt 12.

A controller 66 may control the flow of fluid between the components of the ozone generating system. Electronically controlled valves 68 and pumps 70 controlled by the controller 66 cause the fluid to flow according to the method described above.

In some methods of use, ozonated water in the second tank 60 is used while water in the first tank 54 is being exposed to ozone gas. In some embodiments, multiple generating systems are used, such that while ozonated water is produced in one system it is being used in another.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method for processing meat products comprising:
 providing a conveyor system having a treating region, a processing region, and a conveyor belt, the conveyor belt traveling from the treating region to the processing region;
 distributing ozonated water over the belt proximate the treating region to deposit an ozonated water film; and
 depositing raw meat products directly onto the ozonated water film proximate the processing region.

2. The method of claim 1, further comprising:
 providing a first reservoir;
 producing ozone gas; and
 introducing water and the ozone gas into the first reservoir to produce the ozonated water.

3. The method of claim 2, further comprising;
 releasing undissolved ozone gas from the first reservoir.

4. The method of claim 3, wherein releasing undissolved ozone gas from the first reservoir occurs about one minute after introducing the ozone gas into the first reservoir.

5. The method of claim 4, further comprising:
 providing a second reservoir;
 emptying ozonated water from the first reservoir into the second reservoir;
 introducing ozone gas into the second reservoir; and
 drawing water from the second reservoir for distribution over the conveyor belt.

6. The method of claim 5, further comprising releasing undissolved ozone gas reservoir.

7. The method of claim 6, wherein the step of releasing undissolved ozone gas reservoir occurs about one minute after introducing ozone gas into the second reservoir.

8. The method of claim 7, wherein the step of drawing water from the second about one minute after introducing ozone gas into the second reservoir.

* * * * *